United States Patent [19]

Nowacki et al.

[11] Patent Number: 4,832,015

[45] Date of Patent: May 23, 1989

[54] PEDIATRIC ASTHMATIC INHALER

[75] Inventors: Christopher Nowacki, Long Grove; Alfred G. Brisson, Kildeer; Exequiel D. Cruz, Arlington Heights, all of Ill.

[73] Assignee: Trudell Medical, London, Canada

[21] Appl. No.: 164,230

[22] Filed: May 19, 1988

[51] Int. Cl.⁴ .............................................. A62B 7/00
[52] U.S. Cl. .......................... 128/205.23; 128/203.29; 128/205.17; 128/206.12
[58] Field of Search ...................... 128/205.23, 203.29, 128/727, 205.17, 206.12

[56] References Cited

U.S. PATENT DOCUMENTS

| | | | |
|---|---|---|---|
| 440,713 | 11/1890 | Krohne et al. | 128/205.23 |
| 2,904,033 | 9/1959 | Shane | 128/205.23 |

FOREIGN PATENT DOCUMENTS

| | | | |
|---|---|---|---|
| 809510 | 12/1936 | France | 128/203.29 |
| 370 | of 1903 | United Kingdom | 128/205.23 |

*Primary Examiner*—Edgar S. Burr
*Assistant Examiner*—Aaron J. Lewis
*Attorney, Agent, or Firm*—Robert M. Wolters

[57] ABSTRACT

A pediatric medication inhaler is provided for cooperation with a medication dispersing cylinder and a supply of medication. The inhaler is a one piece device in the nature of a mask molded of integral plastic or elastomer. The invention is characterized in having a bubble or relatively thin wall projecting from the mask-like device, which bubbler flexes inwardly upon inhalation so that a person providing medication to the infant can watch for inhalation.

7 Claims, 1 Drawing Sheet

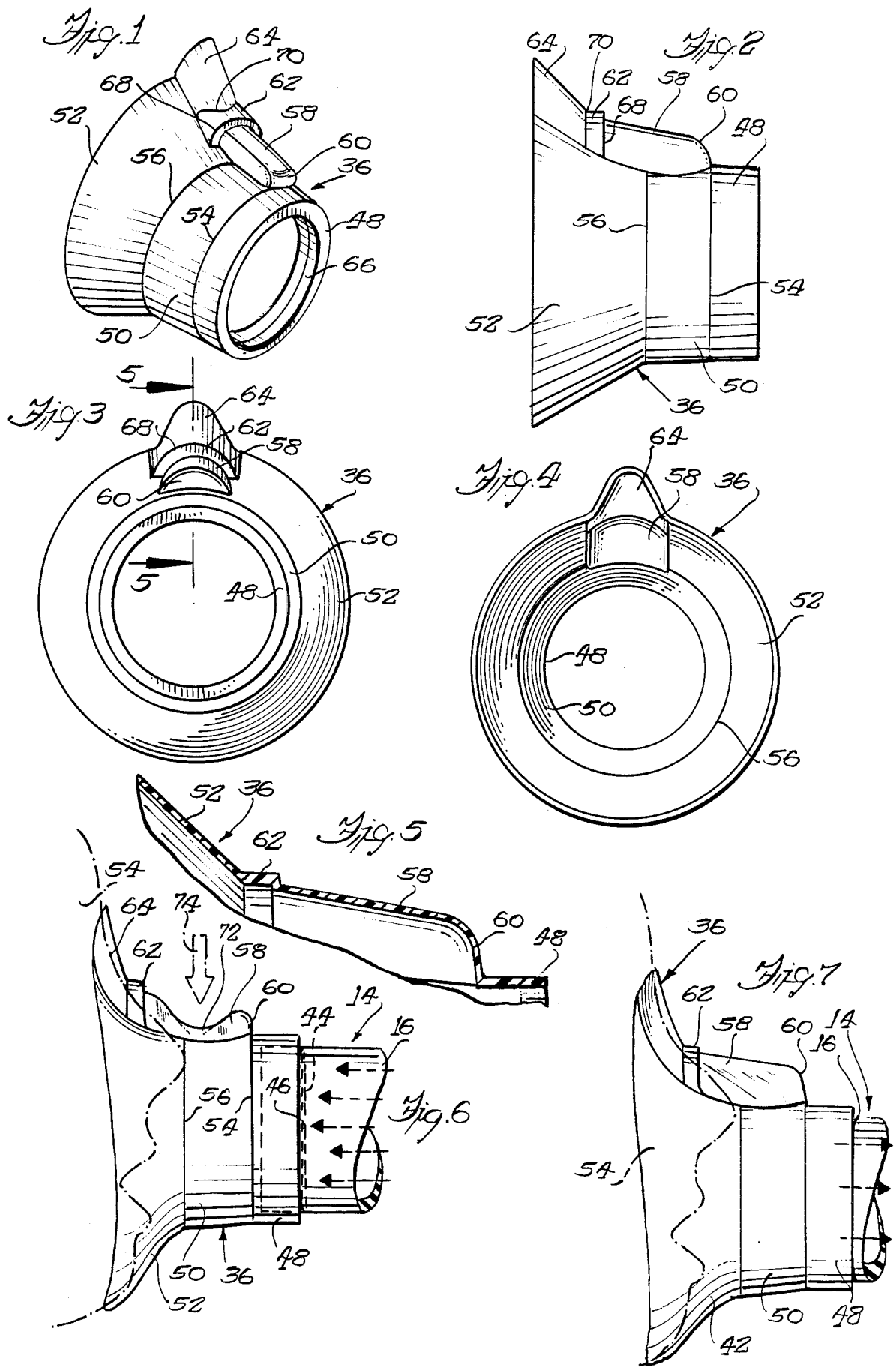

PEDIATRIC ASTHMATIC INHALER

RELATED PATENT APPLICATION

This application comprises an improvement on and is related to the Asthmatic Medication Inhaler shown in the copending application of Christopher Nowacki, Alfred G. Brisson and Exequiel Dela-Cruz entitled "Pediatric Asthmatic Medication Inhaler", Ser. No. 058,683, filed June 4, 1987, said application being a continuation of application Ser. No. 824,529, filed Jan. 31, 1986.

BACKGROUND OF THE INVENTION

A person suffering from Asthma may have rather considerable trouble in breathing when suffering from an asthmatic attack, due to the swelling in the bronchii and due to secretion of mucous. There are various anti-asthmatic pills that are effective, which generally are somewhat slow acting. There are also medications available for intravenous treatment which work quite rapidly, but which require administration by skilled medical personnel. For most patients the promptest, immediately available relief is by way of an inhalant. Epinephrine or other suitable asthmatic medication is packaged with a suitable diluent in a small pressurized canister or cartridge which interfits with a mouthpiece. The patient places the mouthpiece in his mouth, and depresses the cartridge, thereby releasing a measured amount of medication which is inhaled through the mouthpiece.

Some patients do not inhale properly, and the mouthpiece may not be completely effective in cooperation with the cartridge to convert the medication into a mist which is deposited in the proper bronchial area to relieve the asthmatic attack. Often there are small droplets, rather than a mist, and this may be compounded by improper inhalation which results in much of the medication simply going into the throat and stomach where it is ineffective against the asthmatic attack.

In the prior U.S. Pat. No. 4,470,412 in the names of Christopher Nowacki and Alfred G. Brisson, there is disclosed a remarkably efficient and low cost inhalation valve in the nature of an extended mouthpiece for a broncho dialator which aids the asthmatic sufferer in properly inhaling, and in breaking up droplets into a mist form. This inhalation valve has achieved extensive commercial success.

The inhalation valve as discussed above is for use by a patient who can take the mouthpiece thereof into his mouth and inhale and exhale through the mouthpiece. Infants, including babies and small children, cannot be relied upon properly to hold the mouthpiece in the mouth, and indeed, the infant's mouth may be too small for the mouthpiece. Furthermore, it cannot be ascertained with certainty under some conditions whether a baby or small child is properly inhaling and exhaling.

In application Ser. No. 058,683, referenced above, there is disclosed a pediatric asthmatic inhaler which includes a mask-like adaptor fitting over the infant's mouth and nose and sealing to the face, whereby breathing by the infant effects proper inhalation, and exhalation through the valve. A whistle-like device is provided in the adaptor which generates sound upon either or both inhalation and exhalation, whereby a party applying the inhalation valve and medication to an infant may be sure that the medication is being breathed in. This prior pediatric asthmatic medication inhaler works satisfactorily under most conditions. However, for an infant, particularly a baby, in which the volume of inhalation or exhalation may be rather small, and wherein the inhalation or exhalation might also be rather weak, the sound generated is not very loud. Under some circumstances in a noisy environment it may be difficult to hear the sound, and with very low-level respiration the whistle may fail to generate any audible sound. The tapered foam molding of the inhaler requires a rather expensive mold, and the whistle must be inserted as a separate manufacturing step, or requires sophisticated molding techniques if the whistle is to be molded in place.

OBJECTS AND SUMMARY OF THE PRESENT INVENTION

It is an object of the present invention to provide an improved pediatric asthmatic inhaler which is less expensive to produce, which provides a more positive indication of inhalation and expiration, and which is longer lasting.

More particularly, it is an object of the present invention to provide such an inhaler made of flexible plastic material, and having a "bubble" of relatively thin, integral construction which is normally convex outwardly upon exhalation or rest, but which deflects inwardly upon inhalation.

In accordance with the present invention, there is provided an inhalation device similar to and incorporating the advantages of the pediatric asthmatic medication inhaler disclosed in application Ser. No. 058,683 incorporating a mask-like adaptor which fits over the nose and mouth of an infant. The adaptor is molded of flexible, resilient plastic material having sections of uniform thickness, and further including an integral bubble. The bubble is normally convex outwardly, and retains its shape upon exhalation or rest. However, upon inhalation, even of a small degree, the bubble will flex inwardly, where by the adult administering the device may readily observe it visually. The plastic material is of uniform consistency free of bubbles. I.e., it is not a foam, and thereby it is simpler and quicker in molding.

THE DRAWINGS

The invention will best be understood with reference to the following text when taken in connection with the accompanying drawings wherein:

FIG. 1 is a perspective view of an improved pediatric asthmatic inhaler constructed in accordance with the present invention;

FIG. 2 is a side view thereof;

FIG. 3 is a right end view thereof;

FIG. 4 is a left end view thereof;

FIG. 5 is a longitudinal sectional view taken substantially along the line 5—5 in FIG. 3;

FIG. 6 is a side view of the inhaler as applied to an infant's face and upon inhalation; and FIG. 7 is a view similar to FIG. 6, but taken upon exhalation.

DETAILED DISCLOSURE OF THE ILLUSTRATED EMBODIMENT

As is well known, and as is summarized in prior U.S. Pat. No. 4,470,412, a small pressurized canister or cartridge, sometimes referred to as a nebulizer, is charged with epinephrine or other suitable anti-asthmatic medication and a suitable diluent, and under pressure. The cartridge fits into a receiving end of a right angle mouthpiece, the opposite end of which is placed in the asthmatic sufferer's mouth. The cartridge is pressed down, being squeezed between the index finger and thumb underlying the mouthpiece. This causes a valve stem in the cartridge to press against the reaction base in the mouthpiece to discharge a measured quantity of medication into the mouthpiece. The discharge is supposed to be in the form of a mist, but in fact often contains small droplets. The patient inhales and the mist passes into the mouth and hopefully into the bronchial tubes to provide asthmatic relief. The patient is then supposed to hold his breath for a short time, and subsequently to inhale slowly through nearly closed lips. However, as noted heretofore, some of the medication may simply be in the form of droplets rather than mist, and the droplets generally are simply swallowed and do not reach the bronchial tubes to effect their intended purpose.

As is disclosed in detail in the aforesaid prior U.S. Pat. No. 4,470,412, the drops can be broken up into a mist, and the patient can be more or less forced to inhale properly through the use of the inhalation valve forming the subject matter of said patent. Only a portion of the valve is shown herein for an understanding in combination with a pediatric adapter or face mark. Such an inhalation valve 14, is shown fragmentarily in FIGS. 6 and 7, and comprises a cylinder 16 preferably molded of a suitable plastic material. The end of the inhalation valve 14 to which the right angle mouthpiece carrying the medication canister is not shown, but this is well-known, and for example is shown in aforesaid U.S. Pat. No. 4,470,412. A resinous plastic or elastomeric diaphragm 44 is disposed adjacent the end of the cylinder 16 and is provided with a horizontal slit 46. A spider (not shown) lies upstream of the diaphragm 44 and backs up the diaphragm so that the diaphragm cannot flex upstream (to the right in FIG. 6) but only downstream upon inhalation. Further details of the diaphragm structure may be seen in aforesaid U.S. Pat. No. 4,470,412, or in copending application No. 058,683.

The pediatric asthmatic inhaler of the present invention is completed by an adaptor or fitting 36 in the nature of a face mask. The adaptor 36 is molded of a soft plastic material of uniform consistency and density, such as silicone rubber. The adaptor 36 is axially open and continuous, and at its entering end has a short section 48 of eternally very shallow taper, and which is internally substantially of cylindrical shape for encircling and gripping the entering end of the inhalation valve 14. A frustoconical section 50 of slightly greater taper than the section 48 flares outwardly from the section 48. Finally, a face engaging portion 52 flares outwardly from the section 50 at a much greater angle. The face engaging portion 52 is adapted to engage the face of an infant 54 in sealing engagement so as to prevent ingress or egress of air between the fitting 36 and the face.

The difference in taper between the sections 48 and 50 is so little that there is scarcely any parting line visible, but one is shown at 54 in the drawings to illustrate the difference in taper. There is a parting line 56 between the center section 50 and the section or flange 52, although this is not so much a definite line as it is a sharply curved or rolled area.

An upstanding bubble or blister 58 extends radially outwardly from the adaptor or fitting 36, being integral therewith, and has a rounded end or nose 60 terminating substantially at the parting line 54. Except for the nose the blister is slightly less than a semicylinder and terminates at a short cylindrical section 62 of thickened material affording a shape having a certain degree of stability to the rear end of the bubble or blister 58. From the section 62 an extended portion of the flange 52 extends generally radially outwardly at 64 and lies generally over the ridge of the nose of the infant 54, conforming to the shape of the adjacent portion of the face.

The second and third sections or portions of the adaptor or fitting 36 are of uniform thicknesses save for the bubble, namely, the first portion is thicker. The particular dimensions of a specific example include an inside diameter of the inhalation valve cylinder 16 receiving portion 48 of approximately 1.420 inches. This and other cross sections are substantially circular. The inside of this portion is cylindrical, but the outer surface tapers at 2° to facilitate mold release. The inside may flare outwardly at the entering end to facilitate assembly with the cylinder 16. The thickness of this portion is 0.122 inch. The axial length of this section is 0.375 inch.

The intermediate section 50 has an axial length of 0.618 inch and flares outwardly at 10°. The thickness is 0.090 inch. The internal diameter at the parting line 56 is 1.753 inch.

The final section or flange 52 is also 0.090 inch thick, the axial length is 1.016 inch, and the exit diameter is approximately 2.926 inches, the outward taperbeing 30°. The thickness of the bubble or blister 58 and of the flared nosepiece 64 is 0.006 inch. The thickness of the intermediate strengthening portion 62 is 0.078 inch at the forward shoulder 62 thereof, and tapers to a junction with the flared nosepiece 64, with the same thickness thereof, such junction hereinafter being identified by the numeral 70. The bubble 58, including the rounded nose 60 thereof is approximately 0.973 inch in length axially of the adaptor or fitting 36 and forwardly of the shoulder 68. The bubble is 0.762 inch in width, and the rounded end has a radius of 0.375 inch in profile.

Silicone rubber is inert and causes no skin irritation, and can be autoclaved or otherwise heat sterilized without deterioration. The materials are translucent so the infant's nose and mouth can be seen. Wall thickness and hardness in a range of 50–65 durometer are optimized for shape retention and conformability to the infant's face.

As is shown in FIGS. 6 and 7, the rear portion or flange 52 adapts by flexing to accommodate fully to the face of the infant 54, even though the adaptor or fitting 36 might be used on infants of rather substantially different sizes. The flange forms an airtight seal with the face. Thus, when the patient is exhaling, or is resting between breaths, the bubble extends outwardly as shown in FIG. 7. However, when the patient inhales as shown in FIG. 6 the decreased pressure within the adaptor causes the bubble to deflect inwardly as at 72 under the pressure of exterior ambient air as indicated by the arrow 74. It is thus easy for the person administering the medication to observe inhalation, even in a noisy environment. The shiny exterior appearance of the plastic material allows the deflection to be seen even in rather dim light.

Reference has been made to asthmatic medication, but it will be apparent that other medications could be inhaled with the present invention.

The specific example is for illustrative purposes only. Various changes will no doubt occur to those skilled in the art, and will be understood as forming a part of the invention insofar as they fall within the spirit and scope of the appended claims.

The invention is claimed as follows:

1. A pediatric medication inhaler comprising an integral mask-like device molded of flexible plastic material or the like having a central through-opening and including a first portion adapted to grip a cylinder in which medication is dispersed, a second portion of shallow taper and extending from said first portion, a third frusto-conical portion of substantially greater taper extending from said second portion and adapted to fit snugly against an infant's face covering the mouth and nose, said third portion having an integral wedge-shaped outward extension for accommodating the infant's nose, an outwardly projecting bubble integral with said second portion, said second portion having a wall of predetermined thickness and said bubble having a wall that is substantially thinner than the predetermined thickness of said wall of said second portion for enhanced flexibility, whereby said bubble flexes inwardly upon inhalation by said infant for visual observation by an attendant of such inhalation.

2. A pediatric medication inhaler as set forth in claim 1 wherein said bubble extends onto said third portion.

3. A pediatric medication inhaler as set forth in claim 2 wherein said third portion has a wall of set thickness, and further including a rim adjacent the edge of said bubble joining said bubble to said third portion and of greater thickness than said third portion wall for enhanced rigidity at that location.

4. A pediatric medication inhaler as set forth in claim 2 wherein said inhaler has an axial length, said bubble being axially elongated and having a rounded nose at the end thereof on said second portion.

5. A pediatric medication inhaler as set forth in claim 1 wherein said third portion has a wall of preset thickness and adapted to conform to an infant's face, and the wedge-shaped extension is of lesser thickness than said third portion wall thickness for further enhanced flexibility for conforming to an infant's nose and the adjacent portion of its face.

6. A pediatric medication inhaler as set forth in claim 1 wherein the said first portion has a wall of thickness greater than said predetermined thickness for enhanced dimensional stability for gripping a medication dispersing cylinder.

7. A pediatric medication inhaler as set forth in claim 1 wherein the inhaler comprises a one-piece molding of silicone rubber.

* * * * *